(12) United States Patent
Melker et al.

(10) Patent No.: US 10,729,334 B2
(45) Date of Patent: Aug. 4, 2020

(54) METHODS AND SYSTEMS FOR DETERMINING EFFECTIVENESS OF RESPIRATION IN INDIVIDUALS

(71) Applicant: XHALE ASSURANCE, INC., Gainesville, FL (US)

(72) Inventors: Richard J Melker, Newberry, FL (US); Sean Cohen, Gainesville, FL (US); Huwei Tan, Woburn, MA (US)

(73) Assignee: XHALE ASSURANCE, INC, Gainesville, FL (US)

( * ) Notice: Subject to any disclaimer, the term of this patent is extended or adjusted under 35 U.S.C. 154(b) by 201 days.

(21) Appl. No.: 15/111,430

(22) PCT Filed: Jan. 13, 2015

(86) PCT No.: PCT/US2015/011235
§ 371 (c)(1),
(2) Date: Jul. 13, 2016

(87) PCT Pub. No.: WO2015/106280
PCT Pub. Date: Jul. 16, 2015

(65) Prior Publication Data
US 2016/0338597 A1 Nov. 24, 2016

Related U.S. Application Data

(63) Continuation-in-part of application No. 14/512,425, filed on Oct. 11, 2014.

(60) Provisional application No. 61/926,434, filed on Jan. 13, 2014, provisional application No. 61/889,582, filed on Oct. 11, 2013.

(51) Int. Cl.
*A61B 5/00* (2006.01)
*A61B 5/08* (2006.01)
*A61B 5/024* (2006.01)
*A61B 5/083* (2006.01)
*A61B 5/087* (2006.01)
*A61B 5/145* (2006.01)
*A61M 16/10* (2006.01)
(Continued)

(52) U.S. Cl.
CPC .......... *A61B 5/0205* (2013.01); *A61B 5/0816* (2013.01); *A61B 5/0826* (2013.01); *A61B 5/0836* (2013.01); *A61B 5/14551* (2013.01); *A61B 5/7246* (2013.01); *A61B 5/7282* (2013.01); *A61B 5/746* (2013.01); *A61B 5/02416* (2013.01); *A61B 5/0878* (2013.01); *A61B 5/14542* (2013.01); *A61B 5/6819* (2013.01); *A61B 2562/0247* (2013.01); *A61M 16/1005* (2014.02)

(58) Field of Classification Search
CPC .................................................. A61B 5/0826
See application file for complete search history.

(56) References Cited

U.S. PATENT DOCUMENTS 7,177,686 B1    2/2007 Turcott
7,318,808 B2 *  1/2008 Tarassenko .......... A61B 5/0816
                                                          600/529

(Continued)

*Primary Examiner* — John R Downey

(57) ABSTRACT

The present invention relates to systems and methods for comparing photoplethysmography (PPG) signals from an individual with signals from a secondary respiration sensor secured to the individual to determine whether effective respiration has occurred or whether the individual has apnea, hypopnea, or other respiratory distress.

10 Claims, 5 Drawing Sheets

(51) Int. Cl.
   *A61B 5/0205* (2006.01)
   *A61B 5/1455* (2006.01)

(56) References Cited

U.S. PATENT DOCUMENTS

| | | | |
|---|---|---|---|
| 8,430,817 B1* | 4/2013 | Al-Ali | A61B 5/7221 600/301 |
| 8,740,806 B2* | 6/2014 | Parfenova | A61B 5/4818 600/484 |
| 9,095,307 B2* | 8/2015 | Parfenova | A61B 5/4818 |
| 2007/0027375 A1* | 2/2007 | Melker | A61B 5/0873 600/340 |
| 2008/0302364 A1 | 12/2008 | Garde | |
| 2010/0016694 A1 | 1/2010 | Chewe et al. | |
| 2010/0312075 A1* | 12/2010 | McGonigle | A61B 5/0816 600/301 |
| 2013/0133655 A1 | 5/2013 | Kimm | |
| 2013/0172759 A1* | 7/2013 | Melker | A61B 5/14551 600/476 |
| 2014/0005557 A1 | 1/2014 | Rich | |
| 2014/0128697 A1 | 5/2014 | Parfenova et al. | |
| 2014/0275938 A1* | 9/2014 | Addison | A61B 5/0873 600/407 |
| 2015/0038810 A1* | 2/2015 | Melker | A61B 5/0295 600/323 |

* cited by examiner

| | | PPG | | | | |
|---|---|---|---|---|---|---|
| | | High Amplitude | Normal Amplitude | Low Amplitude | Varying Amplitude | Minimal Signal |
| Thermistor | High Amplitude (200% of baseline) | Hyperpnea with increased effort (e.g., from neurological disorders, anxiety, exertion, altitude) | Hyperpnea with normal effort (e.g., anxiety, exertion, altitude) | Artifact (poor signal) | Artifact (poor signal) | Artifact (poor signal) |
| | Normal Amplitude | Normal ventilation with increased effort (e.g., from neurological disorders, anxiety, exertion, altitude) | Normal breathing | Normal breathing (e.g., from sleeping, relaxing, conscious sedation) | Disordered/Ataxic breathing, snoring | Artifact (poor signal) |
| | Low Amplitude (<25% of baseline) | Hypopnea with increased effort (e.g., from asthma, COPD, neurological disorders), nasal cycling, mouth breathing | Hypopnea, nasal cycling, mouth breathing | Hypopnea with decreased effort (e.g., from neurological conditions, sedation [e.g. drug overdose]) | Partial obstruction with low tidal volume (e.g., from snoring, nasal cycling, sedation) | Hypopnea/Respiratory failure (e.g., neurological condition, sedation [e.g. from drug overdose]) |
| | Varying Amplitude | Increased effort with variable tidal volume/partial obstruction (e.g., from neurological condition, snoring, anxiety) | Artifact/nasal cycling, intermittent mouth breathing | Hypopnea/Respiratory failure (e.g., neurological conditions, sedation [e.g. from drug overdose]) | Disordered/Ataxic breathing (e.g., neurological conditions, sedation [e.g. from drug overdose]) | Hypopnea/Respiratory failure (e.g., neurological conditions, sedation [e.g. from drug overdose]) |
| | Minimal signal | High respiratory effort with obstruction | Normal respiratory effort with obstruction | Hypopnea/Respiratory failure (e.g., neurological conditions, sedation [e.g. from drug overdose]) | Disordered/Ataxic breathing with obstruction (e.g., neurological conditions, sedation [e.g. from drug overdose]) | Central apnea (neurological conditions, sedation [e.g., from drug overdose]) |

FIGURE 3

METHODS AND SYSTEMS FOR DETERMINING EFFECTIVENESS OF RESPIRATION IN INDIVIDUALS

CROSS-REFERENCE TO RELATED APPLICATIONS

This application is the 35 USC § 371 national stage application of PCT Application No. PCT/US2015/011235, filed Jan. 13, 2015, which is herein incorporated by reference in its entirety and which also claims priority to, and the benefit of, U.S. Provisional Application No. 61/926,434, filed Jan. 13, 2014, and which is a continuation-in-part of U.S. patent application Ser. No. 14/512,425, filed on Oct. 11, 2014, which claims priority to U.S. Provisional Patent Application 61/889,582, filed Oct. 11, 2013. The contents of each of these applications are incorporated herein by reference in their entirety.

FIELD OF THE INVENTION

The present invention relates to biological sensors, and in particular, to photoplethysmography sensors. The present invention also relates to mammalian respiration and ventilation and methods and devices for monitoring the same.

BACKGROUND OF THE INVENTION

There is a critical unmet need in the field of medicine for non-invasive measurement of respiratory parameters in spontaneously breathing patients. Presently, most respiratory monitoring equipment is used for patients receiving mechanical ventilation. Because most mechanically ventilated patients are intubated, many respiratory parameters can be precisely measured in a way not possible with non-intubated patients. Such parameters include those obtained from capnometry, (end tidal $CO_2$ [$EtCO_2$], respiratory rate and $CO_2$ waveform measurements) and those obtained from respiratory monitors such as differential pressure transducers, absolute pressure transducers and flow transducers (tidal volume [$V_T$], airway pressure [$P_{aw}$], minute ventilation [$V_E$], respiratory rate [RR], respiratory effort/work of breathing [RE/WOB], inspiratory:expiratory ratio [I:E] and deadspace measurements).

Thus, while patients in the OR and ICU may receive intensive respiratory monitoring, similarly reliable monitoring is not presently available for non-intubated patients who are often ambulatory, such as those on general care floors and other areas of the hospital. Numerous organizations, including the U.S. Food and Drug Administration, the American Society of Anesthesiologists, and the Anesthesia Patient Safety Foundation, have noted this lack of monitoring to be problematic and are calling for new technological advances to migrate intensive respiratory monitoring to non-intubated patients. There is also a critical need for improved monitoring of patients receiving patient controlled anesthesia (PCA) since some central nervous system depressants such as opioids may lead to respiratory depression and subsequent morbidity or mortality. Efforts to preemptively identify patients likely to suffer respiratory depression or respiratory arrest have been only partially successful and adequate monitoring solutions are still lacking even if such patients are identified.

SUMMARY OF EMBODIMENTS OF THE INVENTION

Providing according to embodiments of the invention are methods of monitoring the effectiveness of respiration in an individual that include determining whether a respiratory attempt in the individual occurred within a predefined time period based on photoplethysmography (PPG) signals obtained from a PPG sensor secured to the individual; determining whether a ventilation occurred within the predefined time period using a secondary respiration sensor; and comparing the determination of the respiratory attempts based on the PPG signals with the determination of the ventilation based on the secondary respiration sensor to assess whether the individual's respiratory attempts are effective.

Also provided according to embodiments of the invention are systems for monitoring respiration that include a microprocessor configured to compare PPG signals from a PPG sensor secured to an individual with signals from a secondary respiration sensor secured to the individual, to determine at least one of (a) whether ventilation has occurred, (b) whether the patient has central apnea, and (c) whether the patient has obstructive apnea.

BRIEF DESCRIPTION OF THE DRAWINGS

The following drawings are provided to illustrate various aspects of the present inventive concept and are not intended to limit the scope of the present invention unless specified herein.

FIG. 3 provides a table providing likely physiological causes for particular combinations of PPG and thermistor signal readings.

DETAILED DESCRIPTION OF EMBODIMENTS OF THE INVENTION

Figure 1A:
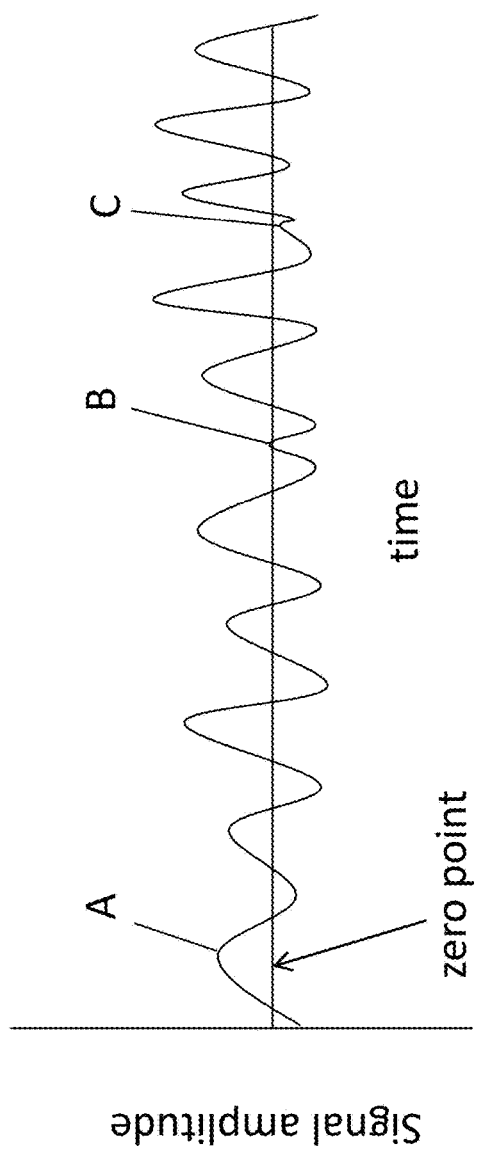
FIGS. 1A and 1B illustrate a zero cross method and a band cross method, respectively, for determining whether a respiratory effort occurred based on the PPG signal.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "on" or "adjacent" to another element, it can be directly on or directly adjacent to the other element or intervening elements may also be present. In contrast, when an element is referred to as being "directly on" or "directly adjacent" to another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers refer to like elements throughout the specification.

It will be understood that, although the terms first, second, etc. may be used herein to describe various elements, these elements should not be limited by these terms. These terms are only used to distinguish one element from another. Thus, a first element discussed below could be termed a second element without departing from the teachings of the present invention.

Provided according to embodiments of the present invention are methods and systems for monitoring the effectiveness of respiratory attempts in individuals. Methods and systems described herein compare the data output from at least one photoplethysmography (PPG) sensor and at least one secondary respiration sensor to determine whether one or more respiratory attempts occurred and whether the attempt(s) resulted in effective ventilation (exchange of oxygen and carbon dioxide). The comparison of the data from the PPG sensor(s) and the secondary respiration sensor(s) may be used to assess whether the individual is suffering from respiratory distress, for example, is apneic (central or obstructive), hypopneic or hyperpneic. The data from multiple sensors may also be used to better correlate the generated signals with the actual physiological processes occurring in the individual.

Definitions

As used herein, an individual, also referred to as a patient, includes any mammal, including humans of any age. The individual may be monitored in any care setting including, but not limited to, hospitals (e.g., operating room (OR), intensive care unit (ICU), general care floors, or during transport therein); nursing homes, medical offices, medical transport and homes.

As used herein, a "raw PPG signal" includes both completely unprocessed signals and those that have been conditioned. In some cases, the raw PPG signals are "conditioned" or filtered before the signal processing methods described herein. In general, such conditioning is achieved by band pass filters, which may filter out undesirably high or low frequency noise in the signal.

As used herein, the term "respiratory attempt" is meant to refer to an attempt by the individual to take a breath, whether or not ventilation occurs. Respiratory attempts imply that the muscles of respiration are contracting in response to signals from the brainstem. The degree of contraction of the respiratory muscles determines the tidal volume ($V_T$) when the airway is patent. If airway obstruction occurs, muscle contraction may result in decreased $V_T$ or in the case of complete obstruction, no airway movement despite muscle contraction. Numerous brainstem inputs including the arterial oxygen saturation ($P_aO_2$), arterial $CO_2$ ($P_aCO_2$) and inputs from various receptors in the respiratory muscles determine the degree of contraction of the respiratory muscles. Disease states (CNS and non-CNS), medications (e.g. opioids, benzodiazepines, etc) and other inputs may alter the "gain" of the brainstem and may decrease or prevent contraction of the respiratory muscles.

As used herein, the term "respiratory air flow/volume" refers to the gas flow/volume in and out of the airways and lungs of an individual, and includes both air flow in the conducting airways (dead space) in the individual's respiratory system and to actual ventilation.

As used herein, "ventilation" is meant to refer to air movement that results in exchange of $CO_2$ and oxygen in the individual. A "ventilation" may also be referred to herein as a "breath".

Photoplethysmography (PPG)

PPG is commonly used for the determination of blood oxygen saturation ($S_PO_2$). This is termed pulse oximetry and is based on the absorption characteristics of red and IR light at different hemoglobin saturations. Because the path length of the light is not fixed, the "ratio of ratios" of the AC and DC components of the two wavelengths is used to calculate $S_PO_2$. In "classic" oxygen saturation measurements, it is assumed that the important information is contained in the "AC" component of the PPG signal and that the DC is only used to determine the "offset" of the signal from the baseline. The inventors have determined that both the AC and DC components of the PPG signals obtained at or on the head (including at the nose or ears), and in particular, at the nasal alae or other sites at or near the nose (e.g., columella, nasal septum, over the ophthalmic artery) contain valuable respiratory information that is unavailable from conventional digit based PPG measurements.

Thus, while in some embodiments of the invention, the raw signals are used to determine the respiratory parameters described herein, in some embodiments of the invention, the PPG signals are separated into AC and/or DC component signal streams, and the isolated AC and/or DC signal stream may be used to monitor respiration in the individual. In particular embodiments, the DC component stream is used to monitor respiration. The separation of the AC and DC component signal streams may be achieved by a number of different methods, but in some embodiments, the components are separated as discussed in U.S. Pat. No. 8,529,459, which is herein incorporated by reference in its entirety. As another example, in some embodiments, the DC component signal stream is determined by interpolating the peaks of the raw signal stream and interpolating the troughs of the combined signal stream and then averaging the two interpolated lines (interpolated peak line and interpolated trough line) to form the DC component signal stream. Other methods of separating AC and DC components of PPG signals that are known in the art may also be used in some embodiments.

While in some embodiments, only one of the raw, AC and DC component signal streams is monitored to analyze respiration in the individual, in some embodiments, more than one of the raw, AC and DC component signal streams are monitored. One reason for monitoring both the AC and DC component signal streams is that the AC and DC components both may provide information regarding respiration (including respiratory rate, effort, obstruction, and the like) and the strength of each signal may vary based on the position or physiological condition of the individual.

The amplitude of the PPG waveforms (AC, DC and raw) may vary with changes in blood volume reflecting the effects of intrathoracic pressure changes throughout the respiratory cycle on differential volume in the right and left ventricle and therefore the carotid arteries. The changes in the DC (and to a lesser degree that AC) component show the inspiration and expiration of a respiratory effort and thus, a presumed respiration rate (RR) can be calculated based on the respiratory efforts. Body position and the degree of airway obstructions (AO) also affect the amplitude of the AC and DC component signals. For instance, because more blood is present in the head when patients are reclining (prone or supine) or in a head down position, the PPG signal (amplitude) is generally larger and the respiratory efforts are easier to identify. Increased tidal volume and airway obstruction may also lead to larger amplitude of the PPG signals due to the increase in intrathoracic pressure.

The PPG signals may vary with the intrathoracic pressure from an attempted breath, and thus, these PPG signals can be used to measure the frequency of respiratory attempts, and the relative effort associated with each attempt. In the absence of obstruction or ineffective ventilation (only deadspace), the rate of respiratory attempts may correlate with the individual's respiration rate. However, if there is complete airway obstruction (as with obstructive sleep apnea) or ineffective ventilation (only deadspace), there may be more respiratory attempts than effective breaths (ventilation). As such, the number of respiratory attempts is always equal to or greater than the number of breaths.

Therefore, in some embodiments of the present invention, the raw, AC and/or DC component signal streams may be evaluated to determine whether the individual has made a respiratory attempt. In particular embodiments, the DC component signal stream is evaluated to determine if a respiratory effort has occurred. In some embodiments, to make this determination, a computer may evaluate the amplitude of the PPG signal stream over time. As an increase in intrathoracic pressure will cause the amplitude of the PPG signal to increase, upon inhalation the amplitude of the PPG signal should increase. Likewise, upon exhalation, the intrathoracic pressure decreases and the PPG signal decreases. Thus, peaks are generated in the PPG signal when effective or ineffective respiratory efforts occur. Criteria can be set for determining whether an increase and decrease in amplitude is sufficiently large to indicate that a respiratory attempt has occurred. In some cases, the area under the curve or area above the curve, or other similar waveform parameters for a plethysmography waveform may be used, alone or in combination with the amplitude, to determine whether a respiratory attempt has occurred.

Referring to FIG. 1A, a PPG signal stream (e.g., a DC component signal stream) may be evaluated over time. In some embodiments, as the amplitude of the signal over time changes to suggest that a breath has occurred (e.g., increase in amplitude for inspiration followed by a decrease for expiration), a zero cross method may be used to determine whether a respiratory attempt has occurred. In such methods, a zero point (baseline) may be determined and if the PPG signal stream amplitude crosses the zero point twice (once for inspiration and once for expiration), a breath is deemed to have been attempted. Peaks "A" and "B" cross the zero point twice and so are considered to be a respiratory attempts, while peak "C" does not cross the zero point line and so is not considered a respiratory attempt. In some embodiments, the zero point is the average amplitude over some predetermined time range, such as over the previous 1, 2, 5 or 10 minutes. In some cases, once the signal crosses the zero point, the computer may determine whether the signal crossing is statistically valid (e.g., via a t-test) and if not, the process may then be iterated.

Figure 1B:
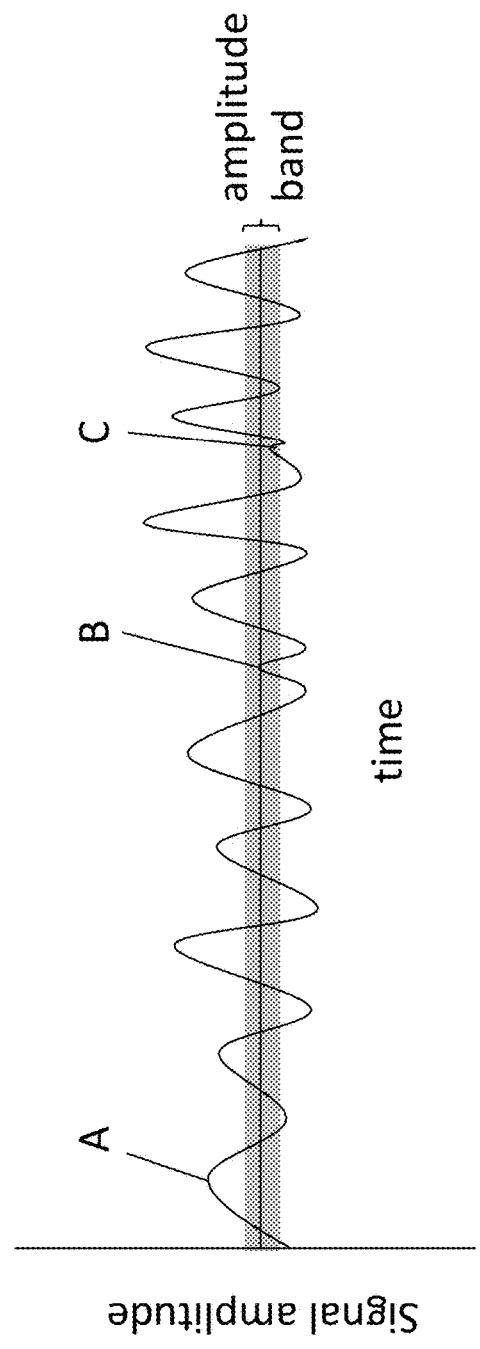
Figure 2:
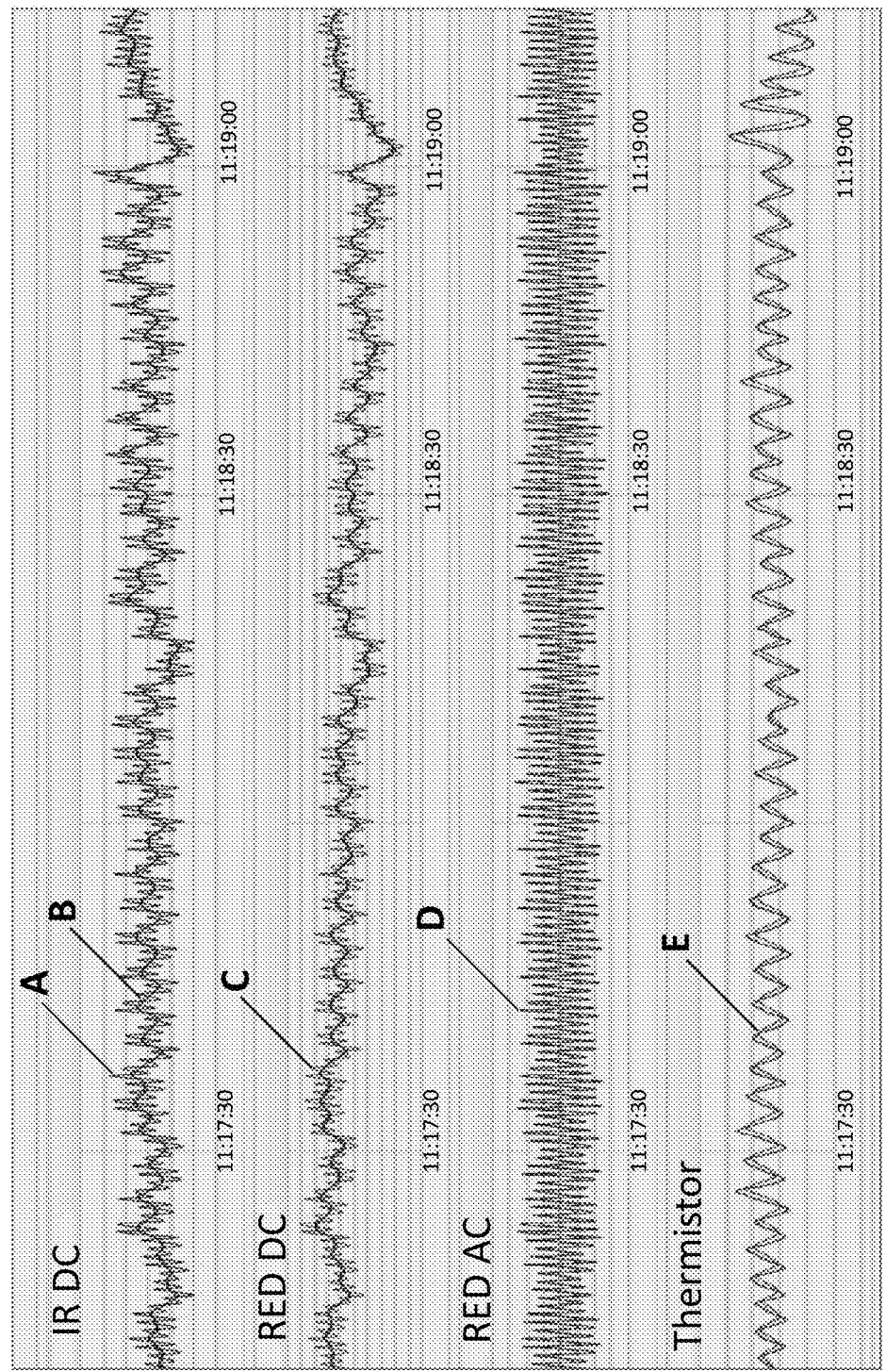
FIG. 2 provides the DC component signal stream obtained from an infrared light emitter (B) and red light emitter (C), along with a red AC component signal stream (D) and a thermistor signal stream (E). The AC and DC component signal streams are obtained from the raw PPG signal (A).

Referring to FIG. 1B, in some embodiments, a "band cross" method may be used such that an amplitude range centered around a zero crossing point may be assigned to the signal, and the size of the band may be determined, for example as fixed amplitude band (e.g., average amplitude+/− a predetermined range) or as a percentage of the total signal amplitude, and in some cases may be determined over a predetermined time range, such as over the previous 1, 2, 5 or 10 minutes. In such cases, a respiratory effort is determined to have occurred when the signal crosses the amplitude band twice (inspiratory effort and expiratory effort). This is analogous to the zero point crossing method but instead of a single point, the signal must cross the amplitude band for a respiratory effort to have been deemed to occur. This decreases the likelihood that noise in the signal will affect the determination of respiratory efforts. In some embodiments, once the signal crosses the amplitude band, the computer may determine whether the signal crossing is statistically valid (e.g., via a t-test) and if not, the process may then be iterated. In FIG. 1B, Peak "A" is deemed to be a respiratory effort, while Peaks "B" and "C" would not be sufficiently large to be deemed respiratory efforts by the band cross method.

In some cases, either alone or in combination with the zero or band cross methods, the magnitude of the increase in signal over the baseline may be used to assess the degree of respiratory effort, which may provide information regarding the presence and degree of obstruction (i.e., a large and/or increasing amplitude may suggest obstruction).

While in general, the methods described herein relate to PPG signals from a central site on or at the head, if a respiratory attempt could be determined from other PPG sensors at the digits or elsewhere on the body, then the methods and systems described herein may be used with PPG signals obtained at any location on the body.

Secondary Respiration Sensors

Secondary respiration sensors may be used to compare with the respiratory information obtained from the PPG sensor(s). Such sensors include, but are not limited to, nasal air flow sensors, nasal pressure sensors, capnometers, thermistors, acoustic sensors, differential pressure transducers, chest or abdominal bands, and the like. In some cases, both the PPG sensor(s) and the secondary respiration sensor(s) are situated at the nose, and in some cases, a single device or system (e.g., an array) may include both the PPG sensor(s) and the secondary respiration sensor(s).

In some embodiments, the secondary respiration sensor may detect respiratory airflow or temperature changes at the nostril, such as with a thermistor. For example, during inspiration, a thermistor placed at the nostril detects a relative decrease in temperature compared to exhalation since, in most situations, body temperature, and therefore exhaled breath temperature, is higher than ambient temperature. Thus, detection of changes in temperature may be a suitable means to determine respiratory air flow and therefore, respiratory rate. Air flow from one or both nostrils may be monitored and compared with the PPG information.

As another example, capnometry may provide a number of respiratory parameters. Such parameters may generally be reliably used for monitoring adequacy of ventilation if the patient is intubated. Unfortunately both hyper- and hypoventilation in patients may cause the results to be unreliable. However, in some cases, capnometry may be useful as a secondary respiration sensor to detect the respiratory airflow and thus, may be helpful to determine whether respiratory attempts lead to effective ventilation.

The respiratory data from the secondary respiration sensor may be handled analogously to the PPG data. As the amplitudes of the secondary respiration sensor signals may change with respiratory air flow during inhalation and exhalation, a zero cross method may be used to measure whether respiratory airflow is sufficient to be deemed ventilation. In such methods, a zero point (baseline) may be determined and if the secondary respiration sensor (e.g., thermistor) signal stream amplitude crosses the zero point twice (once for inspiration and once for expiration), ventilation is deemed to have occurred. If the waveforms in FIG. 1A were thermistor waveforms instead of PPG waveforms, Peaks "A" and "B" cross the zero point twice and so would be considered to be sufficient to result in ventilation, while peak "C" does not cross the zero point line and so would not be considered sufficiently large to indicate ventilation. In some embodiments, the zero point is the average amplitude over some predetermined time range, such as over the previous 1, 2, 5 or 10 minutes. In some cases, once the signal crosses the zero point, the computer may determine whether the signal crossing is statistically valid (e.g., via a t-test) and if not, the process may then be iterated.

In some embodiments, a "band cross" method may be used such that an amplitude range centered around a zero crossing point may be assigned to the signal, and the size of the band may be determined, for example as fixed amplitude band (e.g., average amplitude +/− a predetermined range) or as a percentage of the total signal amplitude, and in some cases may be determined over a predetermined time range, such as over the previous 1, 2, 5 or 10 minutes. In such cases, ventilation is determined to have occurred when the signal crosses the amplitude band twice (inspiratory effort and expiratory effort). In some embodiments, once the signal crosses the amplitude band, the computer may determine whether the signal crossing is statistically valid (e.g., via a t-test) and if not, the process may then be iterated. In the waveform in FIG. 1B was a thermistor waveform instead of a PPG waveform, Peak "A" would be deemed to indicate ventilation, while Peaks "B" and "C" would not be sufficiently large to be ventilation by the band cross method.

In some cases, either alone or in combination with the zero or band cross methods, the magnitude of the increase or decrease in the signal relative to a baseline value may be used to assess the depth of breathing, which may provide information regarding whether hypopnea, apnea or hyperpnea is occurring. For example, if the amplitude of the thermistor or other secondary respiration sensor becomes "high" (e.g., twice a baseline amplitude or greater), then hyperpnea may be indicated. If the amplitude of the thermistor or other secondary respiration sensor becomes "low" (e.g., 25% or less of a baseline amplitude), then hypopnea and or lack of ventilation may be deemed to have occurred.

Methods of Respiratory Monitoring Using PPG and Secondary Respiration Sensors

As described above, a computer may evaluate the PPG data and the secondary respiration sensor(s) data to identify whether there has been an attempted breath (PPG) and whether the respiratory attempt resulted in ventilation (secondary respiration sensor). The combination of the two data streams may also be used to identify physiological processes and problems and to track the respiratory function of the individual.

FIG. 3 provides a list of respiratory processes or problems (and their possible causes), along with how they might be diagnosed by analysis of the PPG and secondary respiration sensor (e.g., a thermistor) signals. In some embodiments, a predetermined reaction may be effected based on which physiological process or problem is indicated by the two signals. For example, medication may be administered (e.g., anti-anxiety agent, narcotic reversal agent, anti-asthma medication, and the like), oxygen may be administered, the patient may be alerted, or medical staff may be alerted.

The ability to distinguish respiratory attempts from effective ventilation may be extremely useful in a clinical setting, both to identify patients in respiratory distress and to decrease false alarms that may be present with other sensors such as thermistors or capnomters (when used by themselves). While this analysis may be on a breath-to-breath basis, analysis of the trend or pattern of breathing over a particular time period may be clinically useful. For example, the total number of respiratory attempts vs. the number of effective breaths for a given time period may be useful to assess the ventilation status of the patient. The percentage of ventilations vs. the total respiratory attempts may be measured at particular time intervals. The trend in this parameter over time may indicate an increase or decrease in the individual's respiratory function. Thus, a predetermined reaction (e.g., alarm, medication or oxygen administration, alerting of individual or staff, etc.) may be effected if the percentage decreases below a certain value. In some cases, a predetermined reaction (e.g., increase or decrease in medication or oxygen) may be effected if the percentage of effective ventilations increases above a certain value.

As a particular example, a patient may be breathing spontaneously with adequate tidal volume to have effective gas exchange. At a later point in time, medication may be administered and/or the patient may fall asleep. At such time, the PPG amplitude and the area under the curve (AUC) may fall while a thermistor shows smaller breaths. The combination of a decrease in the PPG amplitude and the thermistor amplitude are indicative of hypopnea and hypoventilation.

Further, the use of PPG data plus the secondary respiration data can allow for the characterization of obstructive apnea from central apnea. With obstructive apnea, the PPG demonstrates continued and/or increasing respiratory efforts, but the secondary respiration sensor shows less or now air flow indicating the lack of effective ventilation. With central apnea, the PPG signal does not show respiratory attempts and the secondary respiration sensor shows no ventilation in the patient.

Blood oxygen saturation measurements may be used to confirm this determination and may be particularly helpful in defining when an alarm is effected. Research by the inventors has shown that sensors at the nose respond more quickly to decreases in oxygen saturation than sensors placed on digits Thus, sensors on the nose provide an "early warning" of oxygen desaturation (from hypoventilation, atelectasis, or airway obstruction, for example). In the absence of desaturation, changes detected by the PPG and thermistor (or other respiratory sensors) can be trended, thus reducing the number of false alarms, but still providing feedback to healthcare providers that the patient's condition is deteriorating, albeit, at a slower rate. Trend analysis can be particularly valuable in pinpointing the cause of changes in respiration, and in reducing false alarms while providing pertinent information presently unavailable to the healthcare team.

In particular embodiments, respiration may be monitored by comparing the respiration rate from the PPG (e.g, respiratory efforts/min) to respiration rate (e.g., ventilations/min) derived from the secondary respiration sensor. When these rates agree (within a predetermined tolerance), the respiratory attempts are considered successful (ventilation occurs). When these rates diverge such as when the secondary respiration sensor RR decreases by a certain percentage (e.g., 10, 20, 30% or more), then the patient may be considered apneic or hypopneic to the point of hypoventilation or apnea. In some cases, if this divergence lasts longer than a predetermined time period, e.g., 20-30 seconds (the length of time for defined apnea), and in some cases, the saturation has declined (for instance greater than 3%), an alarm is generated (or other predetermined reaction discussed above is effected). In some cases, if the divergence in PPG respiration rate diverges from the respiration rate from the secondary respiration sensor for the predetermined amount of time, but desaturation does not occur, a second predetermined reaction may be generated (e.g., an error message may be generated, additional data is obtained, etc.).

One or more algorithms may be used to combine or fuse the PPG data with the data from the secondary respiration sensor. This algorithm may use multivariate analysis to filter and demodulate physiological signals from the sensors to provide information on the desired parameters. The current quality and trending quality of the input signals may also be measured. One measure of signal quality is the signal to noise ratio (SNR). By monitoring the SNR and establishing a trend of "normal" signal amplitude, an alarm can be set if the SNR ratio decreases below a threshold determined to reflect the point of adequate ventilation.

In some embodiments of the invention, the PPG sensors may be calibrated to obtain more quantitative information regarding the respiratory effort in the individual. A semi-quantitative respiratory effort (work of breathing) can be calculated by calibrating the PPG sensor(s) at the time of placement and periodically thereafter. A surrogate for respiratory effort can be calibrated by having the patient breath through a number of tubes of known resistance (for instance at resistances of 2 cm $H_2O$/L/sec, 10 cm $H_2O$/L/sec and 25 cm $H_2O$/L/sec) at a fixed flow rate (e.g., 15 L/minute) to simulate normal effort, moderately increased effort and markedly increased effort. The patient would inhale through the tubes at a fixed flow rate which, for example, could be easily presented to the patient by placing a reed inside the tube which would provide auditory feedback when the appropriate flow rate is reached. While the patient breaths through the tubes, the PPG amplitude, AUC and AC and DC derived parameters would be measured.

Tidal volume could be estimated from a thermistor (or similar nasal air flow, pressure or volume measuring devices) by having the patient inhale a fixed volume of gas using a face mask connected to a bag containing various volumes of air (e.g. 0.25 L, 0.5 L, 1.0 L and 2.0 L). The amplitude and more accurately the AUC of the thermistor signal would be proportional to the tidal volume. Once the system is calibrated, only the PPG and thermistor signals would be needed to continuously monitor the respiratory status of the patient. Calibration could be repeated at regular intervals thereafter.

Systems for Monitoring Respiration

The methods described herein may be performed by any suitable device, such as, for example, a general-purpose microprocessor (which may include one, two or more individual microprocessors). Such a microprocessor may be adapted to execute software, which may include an operating system and one or more applications, as part of performing the functions described herein. In electronic communication with the microprocessor may be a computer memory, such as a read-only memory (ROM), random access memory (RAM), and the like. Any suitable computer-readable media may be used in the system for data storage. Computer-readable media are capable of storing information that can be interpreted by microprocessor. This information may be data or may take the form of computer-executable instructions, such as software applications, that cause the microprocessor to perform certain functions and/or computer-implemented methods. Depending on the embodiment, such computer-readable media may include computer storage media and communication media.

Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In particular embodiments, a microprocessor may determine whether a respiratory attempt has occurred based on the signals from the PPG sensor and whether this attempt is successful based on the signals from the secondary respiration sensor. In particular, the microprocessor may isolate the AC and DC components of the PPG signal (e.g., as discussed supra and by algorithms that may be stored in the computer storage media in electrical communication with the microprocessor). Such AC and DC components may be analyzed (e.g., as discussed supra) to assess whether a respiratory attempt has occurred. The microprocessor may also receive the signal from the secondary respiration detector and process and analyze such signals (e.g., as discussed supra and by algorithms that may be stored in the computer storage media in electrical communication with the microprocessor) to identify whether respiratory air flow occurred, and whether it was sufficiently large to be deemed ventilation.

The microprocessor may also then compare the determination of whether the respiratory attempt has occurred (optionally in combination with the confidence level of the determination). If a respiratory attempt is deemed to have occurred by the PPG sensor and the respiratory airflow detected by the secondary respiration detector is sufficient to be deemed ventilation, in some embodiments, a breath will be deemed to have occurred and the microprocessor will include this data in any monitor function or physiological parameter calculation (e.g., respiration rate). If no respiratory attempt and no ventilation occurs, then no breath is counted. In some cases, this may indicate central apnea and if no breathing occurs for a predetermined amount of time (e.g., for a time in a range of 10 to 20, 30 or 40 seconds), an alarm may sound, oxygen administered or other action may be taken to promote ventilation and/or oxygenation of the individual. For example, the patient may be alerted or stimulated, such as via a wisp of air on the cheek, vibration of a monitor or other devices and methods of rousing the individual from sleep or a respiratory depressed state. The respiration rate may also be calculated for each sensor separately and the respiration rates compared, as discussed supra, whereby a predefined divergence between the two respiration rates may result in a predetermined reaction, such as an alarm, oxygen administration (or as discussed above).

Example 1

Figure 4:
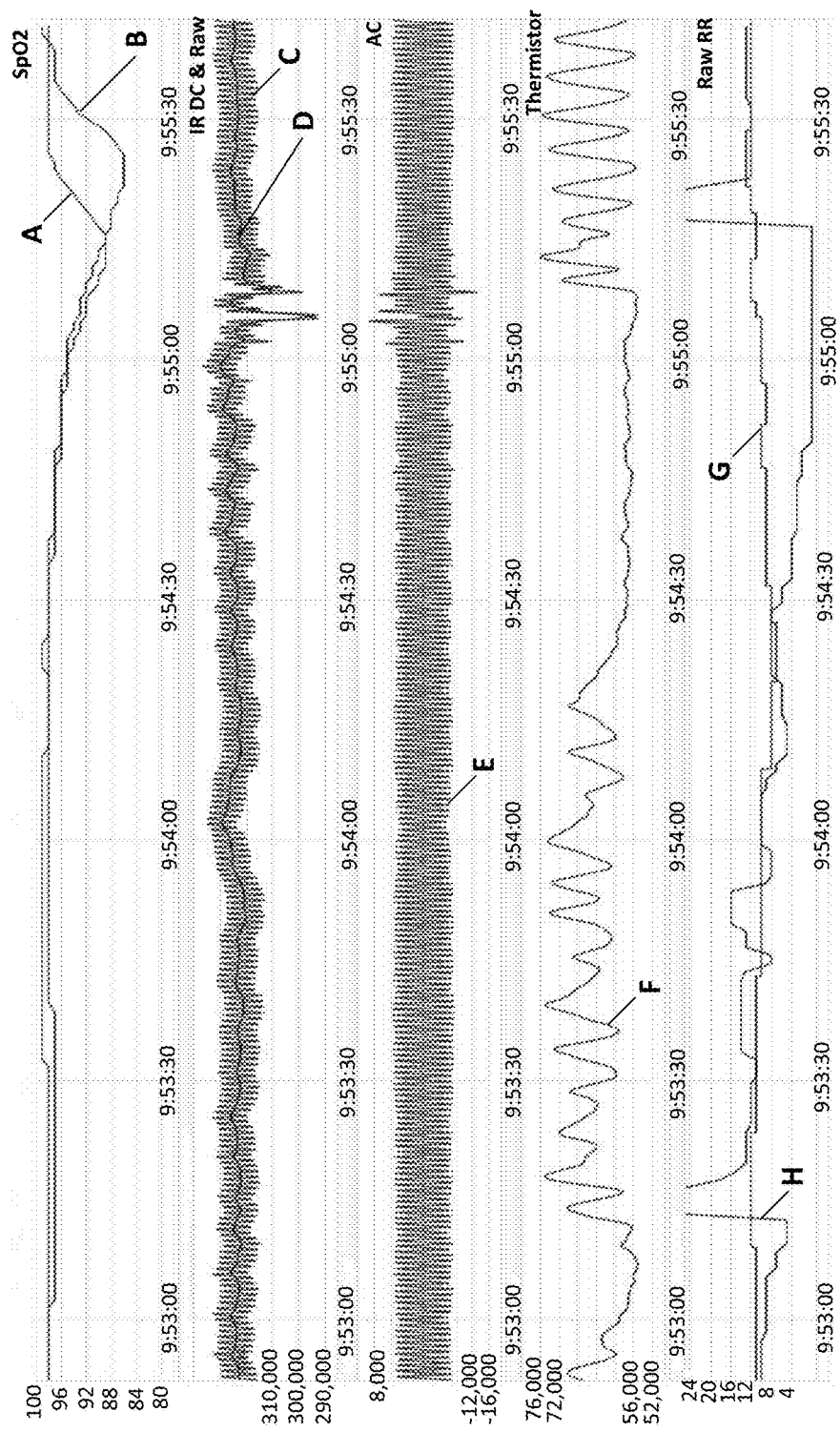
FIG. 4 provides PPG, thermistor and capnometry data over time for a patient in the operating room who is having periods of obstructive apnea typical of obstructive sleep apnea. Signals "A" and "B" show the blood oxygen saturation (SpO2) over time obtained from a patient's nasal alar and finger, respectively. The signal "C" is the raw PPG signal, while signal "D" is the processed DC component of the PPG signal. Signal "E" is the AC component signal. Signal "F" is the thermistor signal (nasal air flow) over time. Signal "G" is the respiration rate over time as determined by the processed AC component of the PPG signal and signal "H" is the capnometry respiratory rate over time.
Figure 5:
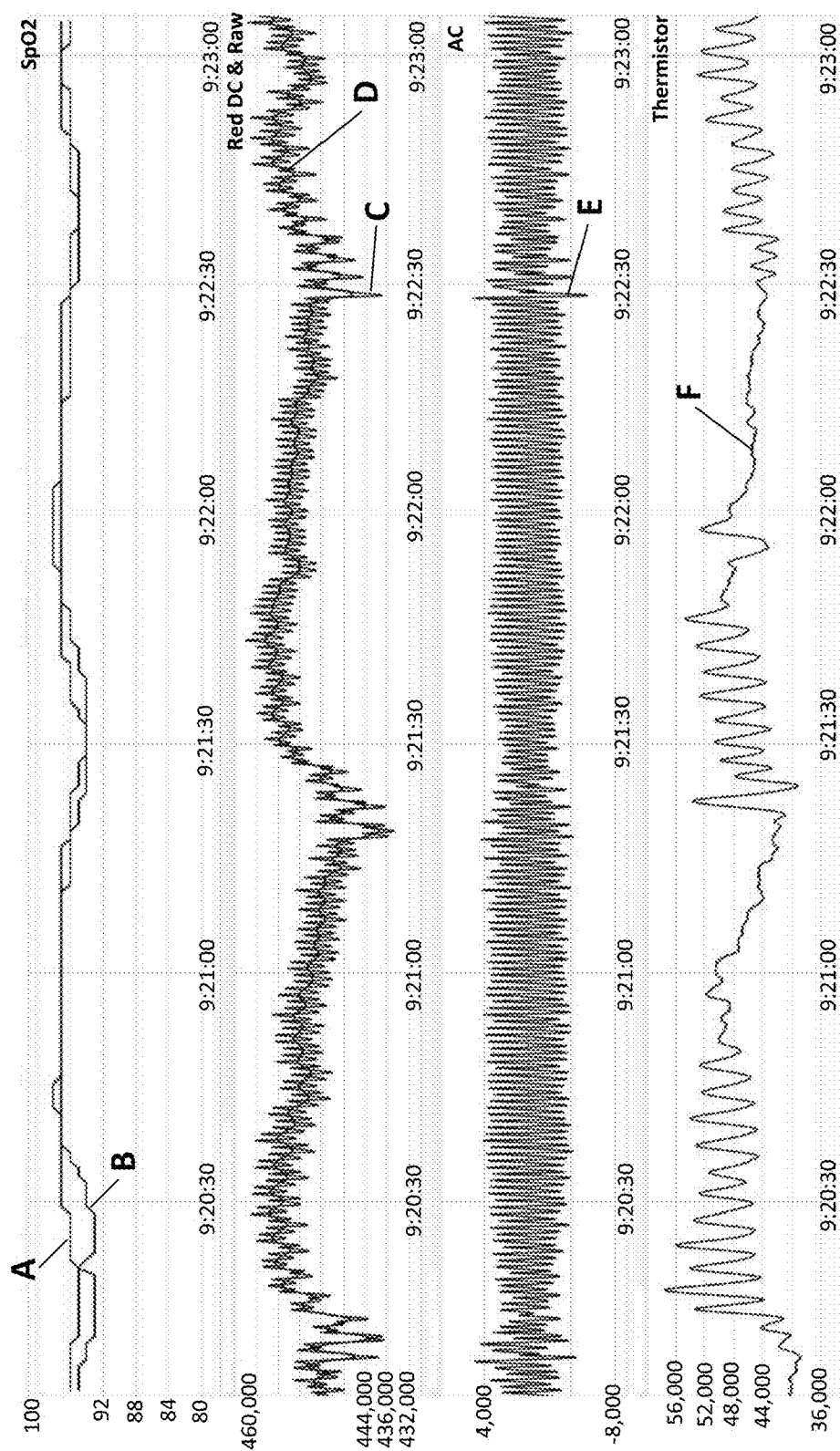
FIG. 5 provides PPG and thermistor data over time for a patient in the operating room who is having periods of obstructive apnea typical of obstructive sleep apnea. Signals "A" and "B" show the blood oxygen saturation ($SpO_2$) over time obtained from a patient's nasal alar and finger, respectively. The signal "C" is the raw PPG signal, while signal "D" is the DC component of the PPG signal. Signal "E" is the AC component signal. Signal "F" is the thermistor signal (nasal air flow) over time.

FIGS. 4 and 5 show the PPG and thermistor signal streams for a patient in the operating room who is having periods of obstructive apnea typical of obstructive sleep apnea. The combination of the PPG data with the thermistor gives a reliable picture of respiratory status of the patient. The PPG provides oxygen saturation over time ("SpO2"), as well as IR DC and Raw and AC waveforms. The thermistor indicates the air flow from the nostrils over time. In this case, the thermistor provides the most reliable data during periods of a patent airway and adequate tidal volume, and the PPG data is more reliable when the patient is partially or completely obstructed (although the signal may work well most of the time and is not affected by obstruction or preferential nasal flow as may be the case with the thermistor) and amplitude is a indicates "effort".

Referring to FIG. 4, waveform "A" denotes the oxygen saturation obtained at the nasal alar, while the "B" waveform denotes oxygen saturation obtained at the finger. It is noted that the desaturation is detected at the nasal alar several seconds before it is detected at the finger. The "C" waveform is the raw PPG signal, while the "D" waveform is the IR DC component signal. The "E" waveform is the AC component signal stream. The "F" waveform is the thermistor waveform. It is noted that when the thermistor loses signal, the IR DC signal becomes more pronounced, the individual increases respiratory efforts against an apparent obstruction. An "arousal" similar after the period of apnea may also be seen in both the PPG signal and where the thermistor signal shows a return to ventilation. Thus, PPG plus thermistor plus oximetry from the nasal ala allows a comprehensive picture of the respiratory status of the patient. As shown in FIG. 4, data from a capnometer (waveform "H", which generates raw respiration rates shown in waveform "G") may also be used with PPG either in combination with or in lieu of the thermistor. Waveforms A-F in FIG. 5 are the same as those identified with respect to FIG. 4.

We claim:

1. A method of monitoring the effectiveness of respiration in an individual, comprising
    obtaining photoplethysmography (PPG) signals from a PPG sensor secured to a nose of the individual over a predefined time period;
    obtaining nasal air flow, nasal pressure or capnometry signals from a nasal air flow, nasal pressure, or capnometry sensor, respectively, secured to the nose of the individual over the predefined time period;
    evaluating an amplitude of the PPG signals over the predefined time period to determine whether the individual attempted respiration;
    evaluating an amplitude of the nasal air flow, nasal pressure or capnometry signals to determine whether a ventilation occurred within the predefined time period;
    comparing the determination of the respiratory attempt during the predetermined time period based on the PPG signals with the determination of the ventilation based on the nasal air flow, nasal pressure or capnometry signals to determine whether the individual's respiratory attempt is effective, and
    calculating a first respiration rate based on the respiratory attempts determined from the PPG signals, calculating a second respiration rate based on ventilations determined from the nasal air flow, nasal pressure or capnometry signals, and if the first and second respiration rates diverge by 10% or more for a predetermined amount of time, a hypopnea or a hyperpnea is determined to have occurred and a predetermined reaction is effected.

2. The method of claim 1, further comprising determining whether the individual's blood oxygen saturation has decreased to a predefined level, and if so, effecting the predetermined reaction.

3. The method of claim 2, wherein the predetermined reaction comprises initiating an alarm.

4. The method of claim 1, wherein the predetermined reaction comprises initiating an alarm.

5. A system for monitoring respiration comprising
    a microprocessor configured to evaluate an amplitude of PPG signals from a PPG sensor on an individual over a predefined time period to determine whether the individual attempted respiration, and to evaluate an amplitude of a nasal air flow, nasal pressure or capnometry signals from a nasal air flow, nasal pressure or capnometry sensor to determine whether ventilation occurred within the predefined time period, and to compare the determination of the respiratory attempt based on the PPG signals with the determination of the ventilation based on the nasal air flow, nasal pressure or capnometry signals to determine whether the individual's respiratory attempt is effective, wherein the microprocessor is further configured to calculate a first respiration rate based on the respiratory attempts determined from the PPG signals, calculate a second respiration rate based on ventilations determined from the nasal air flow, nasal pressure or capnometry signals, and if the first and second respiration rates diverge by 10% or more for a predetermined amount of time, a hypopnea or hyperpnea is determined to have occurred and a predetermined reaction is effected.

6. The system of claim 5, wherein the microprocessor is further configured to isolate an AC and a DC component signal of the PPG signals, use the isolated AC and/or DC component signal to determine whether a respiratory attempt in the individual has occurred.

7. The system of claim 5, wherein the predetermined reaction comprises initiating an alarm.

8. The system of claim 5, wherein the predetermined reaction comprises directing the system to administer oxygen to the individual.

9. The system of claim 5, wherein the microprocessor further determines whether the individual's blood oxygen saturation has decreased a predefined percentage, and the predetermined reaction is effected if hypopnea or hyperpnea has been determined to have occurred and the blood oxygen saturation has decreased a predefined percentage.

10. The system of claim 9, wherein the predefined percentage is in a range of 3 and 10%.

\* \* \* \* \*